(12) United States Patent
Liang et al.

(10) Patent No.: US 11,458,458 B2
(45) Date of Patent: *Oct. 4, 2022

(54) MIXED OXIDES CATALYSTS FOR OXIDATIVE COUPLING OF METHANE

(71) Applicant: Sabic Global Technologies, B.V., Bergen op Zoom (NL)

(72) Inventors: Wugeng Liang, Sugar Land, TX (US); David West, Sugar Land, TX (US); Luanyi Li, Sugar Land, TX (US); Vidya Sagar Reddy Sarsani, Sugar Land, TX (US); Hector Perez, Sugar Land, TX (US); James W. Kauffman, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 349 days.

This patent is subject to a terminal disclaimer.

(21) Appl. No.: 16/495,554

(22) PCT Filed: Mar. 21, 2018

(86) PCT No.: PCT/US2018/023488
§ 371 (c)(1),
(2) Date: Sep. 19, 2019

(87) PCT Pub. No.: WO2018/175533
PCT Pub. Date: Sep. 27, 2018

(65) Prior Publication Data
US 2020/0094224 A1    Mar. 26, 2020

Related U.S. Application Data

(60) Provisional application No. 62/576,515, filed on Oct. 24, 2017, provisional application No. 62/474,804, filed on Mar. 22, 2017.

(51) Int. Cl.
*B01J 23/10* (2006.01)
*B01J 23/00* (2006.01)
(Continued)

(52) U.S. Cl.
CPC ............. *B01J 23/10* (2013.01); *B01J 23/002* (2013.01); *B01J 37/08* (2013.01); *C07C 2/84* (2013.01); *C07C 2523/10* (2013.01)

(58) Field of Classification Search
None
See application file for complete search history.

(56) References Cited

U.S. PATENT DOCUMENTS

| 4,876,409 A | 10/1989 | Leyshon et al. |
| 5,599,510 A * | 2/1997 | Kaminsky ............. B01J 15/005 585/602 |

(Continued)

FOREIGN PATENT DOCUMENTS

| JP | 2012532104 A | 12/2012 |
| WO | 2010117696 A1 | 10/2010 |

(Continued)

OTHER PUBLICATIONS

Sollier, Brenda M. et al., "Oxidative Coupling of Methane on Sr/La2O3 Catalysts: Improving the Catalytic Performance Using Cordierite Monoliths and Ceramic Foams as Structured Substrates," Applied Catalysis A: General, 2017, pp. 65-76, vol. 532, Elsevier.

(Continued)

*Primary Examiner* — Colin W. Slifka
(74) *Attorney, Agent, or Firm* — Rodney B. Carroll; Conley Rose, P.C.

(57) ABSTRACT

An OCM catalyst composition characterized by general formula $A_aLa_bE_cD_dO_x$; wherein A is an alkaline earth metal; wherein E is a first rare earth element; wherein D is a redox agent or a second rare earth element; wherein the first rare (Continued)

earth element and second rare earth element are different; wherein a is 1.0; wherein b is 0.01-10.0; wherein c is 0-10.0; wherein d is 0-10.0; and wherein x balances the oxidation states. The alkaline earth metal is selected from the group consisting of Mg, Ca, Sr, Ba, and combinations thereof. The first rare earth element and the second rare earth element can each independently be selected from the group consisting of Sc, Ce, Pr, Nd, Pm, Sm, Eu, Gd, Y, Tb, Dy, Ho, Er, Tm, Yb, Lu, and combinations thereof. The redox agent is selected from the group consisting of Mn, W, Bi, Sb, Sn, Ce, Pr, and combinations thereof.

20 Claims, 2 Drawing Sheets

(51) Int. Cl.
*B01J 37/08* (2006.01)
*C07C 2/84* (2006.01)

(56) References Cited

U.S. PATENT DOCUMENTS

| | | | |
|---|---|---|---|
| 5,712,217 | A | 1/1998 | Choudhary et al. |
| 6,087,545 | A | 7/2000 | Choudhary et al. |
| 9,446,387 | B2 | 9/2016 | Cizeron et al. |
| 11,091,410 | B2 * | 8/2021 | Liang .................. C07C 2/00 |
| 2014/0107385 | A1 | 4/2014 | Schammel et al. |
| 2016/0023962 | A1 | 1/2016 | Henao et al. |
| 2016/0074844 | A1 | 3/2016 | Freer et al. |
| 2016/0107143 | A1 | 4/2016 | Schammel et al. |
| 2016/0122261 | A1 | 5/2016 | Schammel et al. |

FOREIGN PATENT DOCUMENTS

| | | |
|---|---|---|
| WO | 2016200503 A1 | 12/2016 |
| WO | 2018175533 A1 | 9/2018 |
| WO | 2018175535 A1 | 9/2018 |

OTHER PUBLICATIONS

Conway, S.J. et al., "Comparison of Lanthanum Oxide and Strontium-Modified Lanthanum Oxide Catalysts for the Oxidative Coupling of Methane," Applied Catalysis A: General, 1992, pp. 199-212, vol. 86, Elsevier Science Publishers, BV.

Machida, Ken-Ichi et al., "Oxidative Dimerization of Methane Over Cerium Mixed Oxides and Its Relation With Their Ion-Conducting Characteristics," Journal of the Chemical Society, Chemical Communications, 1987, pp. 1639-1640.

Arndt, Sebastian et al., "A Critical Assessment of Li/MgO-Based Catalysts for the Oxidative Coupling of Methane," Catalysis Reviews; Science and Engineering, 2011, pp. 424-514, vol. 53, Taylor & Francis Group, LLC.

Arndt, Sebastian et al., "Mn—Na2WO4/SiO2 as Catalyst For The Oxidative Coupling of Methane. What is Really Known?," Applied Catalysis A: General, 2012, pp. 53-61, vols. 425-426, Elsevier.

Fang, Xueping et al., "Preparation and Characterization of Catalyst for Oxidative Coupling of Methane," Journal of Molecular Catalysis, 1992, pp. 255-261, vol. 8, No. 4.

Fang, Xueping et al., "Oxidative Coupling of Methane on W—Mn Catalysts," Journal of Molecular Catalysis, 1992, pp. 427-433, vol. 6, No. 6.

Zavyalova, Ulyana et al., "Statistical Analysis of Past Catalytic Data on Oxidative Methane Coupling for New Insights into the Composition of High-Performance Catalysts," ChemCatChem, 2011, pp. 1935-1947, vol. 3, Wiley-VCH Verlag GmbH & Co. KGaA.

Sinev, M. Yu et al., "Kinetics of Oxidative Coupling of Methane: Bridging the Gap Between Comprehension and Description," Journal of Natural Gas Chemistry, 2009, pp. 273-287, vol. 18, Elsevier.

Oshima, K. et al., "Catalytic Oxidative Coupling of Methane with a Dark Current in an Electric Field at Low External Temperature," International Journal of Plasma Environmental Science & Technology, 2012, pp. 266-271, vol. 6, Issue 3.

Choudhary, Vasant et al., "Oxidative Coupling of Methane and Oxidative Dehydrogenation of Ethane over Strontium-Promoted Rare Earth Oxide Catalysts," 1998, Journal of Chemical Technology and Biotechnology, pp. 167-172, vol. 71, SCI.

Foreign communication from related application—International Search Report and Written Opinion of the International Searching Authority, Application No. PCT/US2018/023494, dated Jul. 27, 2018, 15 pages.

Foreign communication from related application—International Search Report and Written Opinion of the International Searching Authority, Application No. PCT/US2018/023488, dated Jul. 25, 2018, 13 pages.

Foreign communication from related application—International Preliminary Report on Patentability, Application No. PCT/US2018/023488, dated Sep. 24, 2019, 9 pages.

Foreign communication from related application—International Preliminary Report on Patentability, Application No. PCT/US2018/023494, dated Sep. 24, 2019, 10 pages.

USPTO Filing Receipt and Specification for Priority U.S. Appl. No. 62/474,804, "Mixed Oxides Catalysts for Oxidative Coupling of Methane", filed Mar. 22, 2017, 44 pages.

USPTO Filing Receipt and Specification for Priority U.S. Appl. No. 62/576,515, "Mixed Oxides Catalysts for Oxidative Coupling of Methane for Adiabatic Processes", filed Oct. 24, 2017, 48 pages.

Leyshon, DW et al., "Thin Bed Reactor for Conversion of Methane to Higher Hydrocarbons," Natural Gas Conversion, 1991, pp. 497-507, Elsevier Science Publishers B.V.

* cited by examiner

ND_STATES## US 11,458,458 B2

MIXED OXIDES CATALYSTS FOR OXIDATIVE COUPLING OF METHANE

CROSS REFERENCE TO RELATED APPLICATIONS

This application is a filing under 35 U.S.C. 371 of International Application No. PCT/US2018/023488 filed Mar. 21, 2018, entitled "Mixed Oxides Catalysts for Oxidative Coupling of Methane" which claims priority to U.S. Provisional Application Nos. 62/474,804 filed Mar. 22, 2017, and 62/576,515 filed Oct. 24, 2017, which applications are incorporated by reference herein in their entirety.

TECHNICAL FIELD

The present disclosure relates to catalyst compositions for oxidative coupling of methane (OCM), more specifically catalyst compositions based on oxides of alkaline earth metals, La, and optionally redox agents and/or rare earth elements for OCM, and methods of making and using same.

BACKGROUND

Hydrocarbons, and specifically olefins such as ethylene, are typically building blocks used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes.

Oxidative coupling of the methane (OCM) has been the target of intense scientific and commercial interest for more than thirty years due to the tremendous potential of such technology to reduce costs, energy, and environmental emissions in the production of ethylene ($C_2H_4$). As an overall reaction, in the OCM, methane ($CH_4$) and oxygen ($O_2$) react exothermically over a catalyst to form $C_2H_4$, water ($H_2O$) and heat.

Ethylene can be produced by OCM as represented by Equations (I) and (II):

$$2CH_4 + O_2 \rightarrow C_2H_4 + 2H_2O \quad \Delta H = -67 \text{ kcal/mol} \quad \text{(I)}$$

$$2CH_4 + \tfrac{1}{2}O_2 \rightarrow C_2H_6 + H_2O \quad \Delta H = -42 \text{ kcal/mol} \quad \text{(II)}$$

Oxidative conversion of methane to ethylene is exothermic. Excess heat produced from these reactions (Equations (I) and (II)) can push conversion of methane to carbon monoxide and carbon dioxide rather than the desired $C_2$ hydrocarbon product (e.g., ethylene):

$$CH_4 + 1.5O_2 \rightarrow CO + 2H_2O \quad \Delta H = -124 \text{ kcal/mol} \quad \text{(III)}$$

$$CH_4 + 2O_2 \rightarrow CO_2 + 2H_2O \quad \Delta H = -192 \text{ kcal/mol} \quad \text{(IV)}$$

The excess heat from the reactions in Equations (III) and (IV) further exasperate this situation, thereby substantially reducing the selectivity of ethylene production when compared with carbon monoxide and carbon dioxide production.

Additionally, while the overall OCM is exothermic, catalysts are used to overcome the endothermic nature of the C—H bond breakage. The endothermic nature of the bond breakage is due to the chemical stability of methane, which is a chemically stable molecule due to the presence of its four strong tetrahedral C—H bonds (435 kJ/mol). When catalysts are used in the OCM, the exothermic reaction can lead to a large increase in catalyst bed temperature and uncontrolled heat excursions that can lead to catalyst deactivation and a further decrease in ethylene selectivity. Furthermore, the produced ethylene is highly reactive and can form unwanted and thermodynamically favored deep oxidation products.

Generally, in the OCM, $CH_4$ is first oxidatively converted into ethane ($C_2H_6$), and then into $C_2H_4$. $CH_4$ is activated heterogeneously on a catalyst surface, forming methyl free radicals (e.g., $CH_3\cdot$), which then couple in a gas phase to form $C_2H_6$. $C_2H_6$ subsequently undergoes dehydrogenation to form $C_2H_4$. An overall yield of desired $C_2$ hydrocarbons is reduced by non-selective reactions of methyl radicals with oxygen on the catalyst surface and/or in the gas phase, which produce (undesirable) carbon monoxide and carbon dioxide. Some of the best reported OCM outcomes encompass a 20% conversion of methane and 80% selectivity to desired $C_2$ hydrocarbons.

There are many catalyst systems developed for OCM processes, but such catalyst systems have many shortcomings. For example, conventional catalysts systems for OCM display catalyst performance problems, stemming from a need for high reaction temperatures. Thus, there is an ongoing need for the development of catalyst compositions for OCM processes.

BRIEF SUMMARY

Disclosed herein is an oxidative coupling of methane (OCM) catalyst composition characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

Also disclosed herein is a method of making an oxidative coupling of methane (OCM) catalyst composition comprising (a) forming an OCM catalyst precursor mixture; wherein the OCM catalyst precursor mixture comprises one or more compounds comprising an alkaline earth metal cation, one or more compounds comprising a La cation, one or more compounds comprising a first rare earth element cation, and one or more compounds comprising a redox agent cation or a second rare earth element cation; wherein the first rare earth element cation and the second rare earth element cation are different; wherein the OCM catalyst precursor mixture is characterized by a molar ratio of La to alkaline earth metal of b:1, wherein b is from about 0.01 to about 10.0; wherein the OCM catalyst precursor mixture is characterized by a molar ratio of first rare earth element to alkaline earth metal of c:1, wherein c is from about 0 to about 10.0; and wherein the OCM catalyst precursor mixture is characterized by a molar ratio of redox agent or second rare earth element to alkaline earth metal of d:1, wherein d is from about 0 to about 10.0; and (b) calcining at least a portion of the OCM catalyst precursor mixture to form the OCM catalyst composition, wherein the OCM catalyst composition is characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

Further disclosed herein is a method of making an oxidative coupling of methane (OCM) catalyst composition comprising (a) forming an OCM catalyst precursor aqueous solution comprising an alkaline earth metal nitrate, a La nitrate, a first rare earth element nitrate, and a redox agent nitrate or a second rare earth element nitrate; wherein the first rare earth element nitrate and the second rare earth element nitrate are different; wherein the OCM catalyst precursor aqueous solution is characterized by a molar ratio of La to alkaline earth metal of b:1, wherein b is from about 0.01 to about 10.0; wherein the OCM catalyst precursor aqueous solution is characterized by a molar ratio of first rare earth element to alkaline earth metal of c:1, wherein c is from about 0 to about 10.0; and wherein the OCM catalyst precursor aqueous solution is characterized by a molar ratio of redox agent or second rare earth element to alkaline earth metal of d:1, wherein d is from about 0 to about 10.0; (b) drying at least a portion of the OCM catalyst precursor aqueous solution at a temperature of equal to or greater than about 75° C. to form an OCM catalyst precursor mixture; and (c) calcining at least a portion of the OCM catalyst precursor mixture at a temperature of equal to or greater than about 750° C. to form the OCM catalyst composition, wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

Further disclosed herein is an oxidative coupling of methane (OCM) catalyst composition produced by (a) solubilizing one or more compounds comprising an alkaline earth metal cation, one or more compounds comprising a La cation, one or more compounds comprising a first rare earth element cation, and one or more compounds comprising a redox agent cation or second rare earth element cation in an aqueous medium to form an OCM catalyst precursor aqueous solution; wherein the first rare earth element cation and the second rare earth element cation are different; wherein the OCM catalyst precursor aqueous solution is characterized by a molar ratio of La to alkaline earth metal of b:1, wherein b is from about 0.01 to about 10.0; wherein the OCM catalyst precursor aqueous solution is characterized by a molar ratio of first rare earth element to alkaline earth metal of c:1, wherein c is from about 0 to about 10.0; and wherein the OCM catalyst precursor aqueous solution is characterized by a molar ratio of redox agent or second rare earth element to alkaline earth metal of d:1, wherein d is from about 0 to about 10.0; (b) drying at least a portion of the OCM catalyst precursor aqueous solution at a temperature of equal to or greater than about 75° C. to form an OCM catalyst precursor mixture; and (c) calcining at least a portion of the OCM catalyst precursor mixture at a temperature of equal to or greater than about 750° C. to form the OCM catalyst composition, wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

Further disclosed herein is a method for producing olefins comprising (a) introducing a reactant mixture to a reactor comprising an oxidative coupling of methane (OCM) catalyst composition; wherein the reactant mixture comprises methane ($CH_4$) and oxygen ($O_2$); wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states; (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture.

BRIEF DESCRIPTION OF THE DRAWINGS

For a detailed description of the preferred aspects of the disclosed methods, reference will now be made to the accompanying drawing in which.

DETAILED DESCRIPTION

Figure 1:
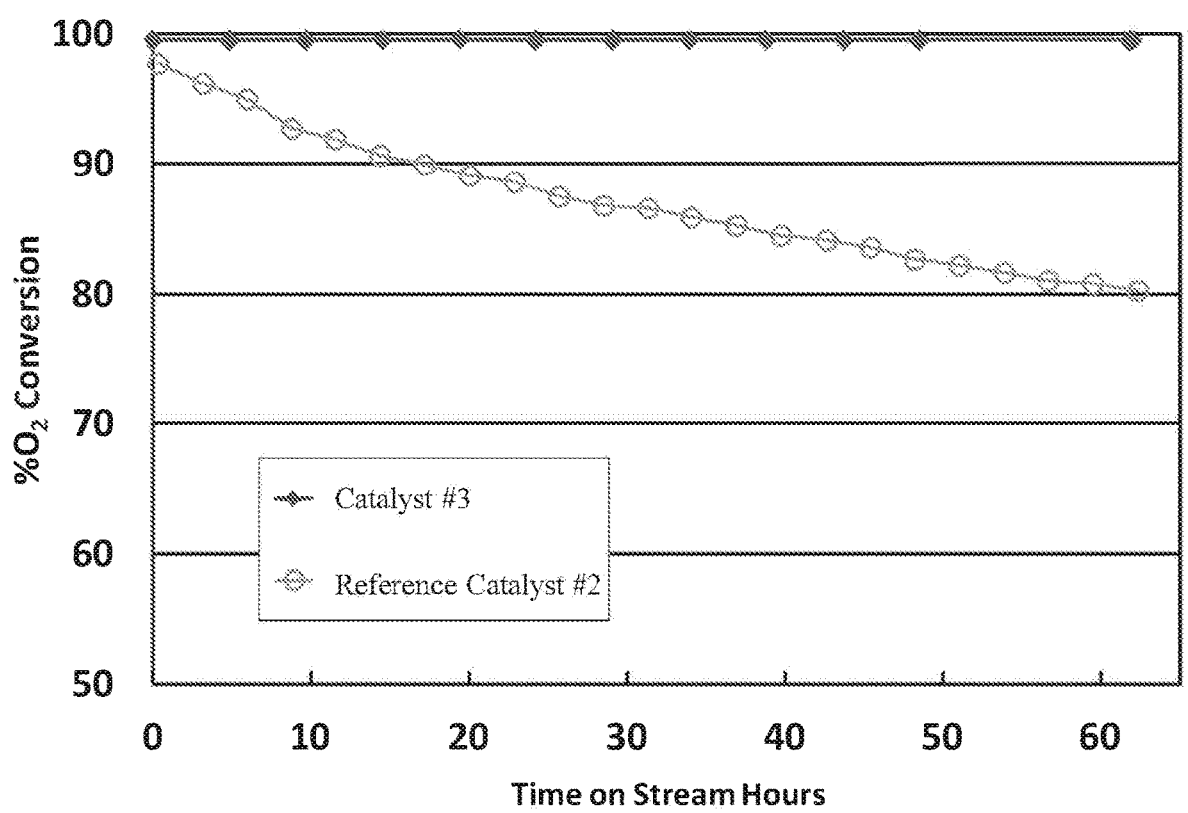
FIG. 1 displays a graph of $O_2$ conversion in an OCM reaction over time for different catalysts.

Disclosed herein are oxidative coupling of methane (OCM) catalyst compositions and methods of making and using same. In an aspect, an OCM catalyst composition can be characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

A method of making an OCM catalyst composition can generally comprise the steps of (a) forming an OCM catalyst precursor mixture; wherein the OCM catalyst precursor mixture comprises one or more compounds comprising an alkaline earth metal cation, one or more compounds comprising a La cation, one or more compounds comprising a first rare earth element cation, and one or more compounds comprising a redox agent cation or a second rare earth element cation; wherein the first rare earth element cation and the second rare earth element cation are different; wherein the OCM catalyst precursor mixture is characterized by a molar ratio of La to alkaline earth metal of b:1, wherein b is from about 0.01 to about 10.0; wherein the OCM catalyst precursor mixture is characterized by a molar ratio of first rare earth element to alkaline earth metal of c:1, wherein c is from about 0 to about 10.0; and wherein the OCM catalyst precursor mixture is characterized by a molar ratio of redox agent or second rare earth element to alkaline earth metal of d:1, wherein d is from about 0 to about 10.0; and (b) calcining the OCM catalyst precursor mixture to form the OCM catalyst composition, wherein the OCM catalyst composition is characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states. The one or more compounds comprising an alkaline earth metal cation can comprise an alkaline earth metal nitrate, an alkaline earth metal oxide, an alkaline earth metal hydroxide, an alkaline earth metal chloride, an alkaline earth metal acetate, an alkaline earth metal carbonate, and the like, or combinations thereof; the one or more compounds comprising a La cation can comprise a La nitrate, a La oxide, a La hydroxide, a La chloride, a La acetate, a La carbonate, and the like, or combinations thereof; the one or more compounds comprising a first rare earth element cation can comprise a first rare earth element nitrate, a first rare earth element oxide, a first rare earth element hydroxide, a first rare earth element chloride, a first rare earth element acetate, a first rare earth element carbonate, and the like, or combinations thereof; the one or more compounds comprising a redox agent cation can comprise a redox agent nitrate, a redox agent oxide, a redox agent hydroxide, a redox agent chloride, a redox agent acetate, a redox agent carbonate, and the like, or combinations thereof; and the one or more compounds comprising a second rare earth element cation can comprise a second rare earth element nitrate, a second rare earth element oxide, a second rare earth element hydroxide, a second rare earth element chloride, a second rare earth element acetate, a second rare earth element carbonate, and the like, or combinations thereof.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

In an aspect, a method for producing olefins as disclosed herein can comprise introducing a reactant mixture to a reactor comprising an oxidative coupling of methane (OCM) catalyst composition to form a product mixture comprising olefins, wherein the reactant mixture comprises methane ($CH_4$) and oxygen ($O_2$), and wherein the OCM catalyst composition can be characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

The reactant mixture can be a gaseous mixture. The reactant mixture can comprise a hydrocarbon or mixtures of hydrocarbons, and oxygen. In some aspects, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an aspect, the reactant mixture can comprise $CH_4$ and $O_2$.

The $O_2$ used in the reactant mixture can be oxygen gas (which may be obtained via a membrane separation process), technical oxygen (which may contain some air), air, oxygen enriched air, and the like, or combinations thereof.

The reactant mixture can further comprise a diluent. The diluent is inert with respect to the OCM reaction, e.g., the diluent does not participate in the OCM reaction. In an aspect, the diluent can comprise water, nitrogen, inert gases, and the like, or combinations thereof.

The diluent can provide for heat control of the OCM reaction, e.g., the diluent can act as a heat sink. Generally, an inert compound (e.g., a diluent) can absorb some of the heat produced in the exothermic OCM reaction, without degrading or participating in any reaction (OCM or other reaction), thereby providing for controlling a temperature inside the reactor.

The diluent can be present in the reactant mixture in an amount of from about 0.5% to about 80%, alternatively from about 5% to about 50%, or alternatively from about 10% to about 30%, based on the total volume of the reactant mixture.

A method for producing olefins can comprise introducing the reactant mixture to a reactor, wherein the reactor comprises the OCM catalyst composition disclosed herein. The reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an aspect, the reactor can comprise an adiabatic reactor. In an aspect, the reactor can comprise a catalyst bed comprising the OCM catalyst composition disclosed herein.

The reactant mixture can be introduced to the reactor at a temperature of from about 150° C. to about 1,000° C., alternatively from about 225° C. to about 900° C., or alternatively from about 250° C. to about 800° C. As will be appreciated by one of skill in the art, and with the help of this disclosure, while the OCM reaction is exothermic, heat input is necessary for promoting the formation of methyl radicals from $CH_4$, as the C—H bonds of $CH_4$ are very stable, and the formation of methyl radicals from $CH_4$ is endothermic. In an aspect, the reactant mixture can be introduced to the reactor at a temperature effective to promote an OCM reaction.

The reactor can be characterized by a temperature of from about 400° C. to about 1,200° C., alternatively from about 500° C. to about 1,100° C., or alternatively from about 600° C. to about 1,000° C.

The reactor can be characterized by a pressure of from about ambient pressure (e.g., atmospheric pressure) to about 500 psig, alternatively from about ambient pressure to about 200 psig, or alternatively from about ambient pressure to about 150 psig. In an aspect, the method for producing olefins as disclosed herein can be carried out at ambient pressure.

The reactor can be characterized by a gas hourly space velocity (GHSV) of from about 500 $h^{-1}$ to about 10,000,000 $h^{-1}$, alternatively from about 500 $h^{-1}$ to about 1,000,00011$^{1}$, alternatively from about 500 $h^{-1}$ to about 500,000 $h^{-1}$, alternatively from about 1,000 $h^{-1}$ to about 500,000 $h^{-1}$, alternatively from about 1,500 $h^{-1}$ to about 500,000 $h^{-1}$, alternatively from about 2,000 $h^{-1}$ to about 500,000 $h^{-1}$, alternatively from about 5,000 $h^{-1}$ to about 500,000 $h^{-1}$, alternatively from about 10,000 $h^{-1}$ to about 500,000 $h^{-1}$, or alternatively from about 50,000 $h^{-1}$ to about 500,000 $h^{-1}$. Generally, the GHSV relates a reactant (e.g., reactant mixture) gas flow rate to a reactor volume. GHSV is usually measured at standard temperature and pressure.

The reactor can comprise an OCM catalyst composition as disclosed herein characterized by the general formula $A_a La_b E_e D_d O_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0, alternatively from about 0.1 to about 8, or alternatively from about 0.5 to about 5; wherein c is from about 0 to about 10.0, alternatively from about 0.1 to about 8, or alternatively from about 0.5 to about 5; wherein d is from about 0 to about 10.0, alternatively from about 0.1 to about 8, or alternatively from about 0.5 to about 5; and wherein x balances the oxidation states. As will be appreciated by one of the skill in the art, and with the help of this disclosure, each of the A, La, E and D can have multiple oxidation states within the OCM catalyst composition, and as such x can have any suitable value that allows for the oxygen anions to balance all the cations. Without wishing to be limited by theory, the different metals (A, La, E, and D) present in the OCM catalyst compositions as disclosed herein display synergetic effects in terms of conversion and selectivity. Further, and without wishing to be limited by theory, different ion radii and valences of the multiple metals (A, La, E, and D) present in the OCM catalyst compositions as disclosed herein can generate formation of uncompensated oxygen vacancies, which can lead to further improvement of catalyst performance, for example in terms of conversion, selectivity, stability, etc.

The OCM catalyst composition as disclosed herein can comprise an alkaline earth metal (A). The alkaline earth metal (A) can be selected from the group consisting of magnesium (Mg), calcium (Ca), strontium (Sr), barium (Ba), and combinations thereof. In an aspect, the alkaline earth metal (A) is strontium (Sr).

The OCM catalyst composition as disclosed herein can comprise a first rare earth element (E) and/or a second rare earth element (D), wherein E and D are different. The first rare earth element (E) and the second rare earth element (D) can each independently be selected from the group consisting of scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

The OCM catalyst composition as disclosed herein can comprise a redox agent (D). As will be appreciated by one of skill in the art, and with the help of this disclosure, D can be either a redox agent or a second rare earth element. The redox agent (D) can be selected from the group consisting of manganese (Mn), tungsten (W), bismuth (Bi), antimony (Sb), tin (Sn), cerium (Ce), praseodymium (Pr), and combinations thereof. A redox agent generally refers to a chemical species that possesses the ability to undergo both an oxidation reaction and a reduction reaction, and such ability usually resides in the chemical species having more than one stable oxidation state other than the oxidation state of zero (0). As will be appreciated by one of skill in the art, and with the help of this disclosure, some rare earth elements, such as Ce and Pr, can also be considered redox agents. Further, as will be appreciated by one of skill in the art, and with the help of this disclosure, when D is Ce and/or Pr, D can be considered either a redox agent or a second rare earth element.

In some aspects, the redox agent (D) is manganese (Mn). In other aspects, the redox agent (D) is tungsten (W).

In an aspect, the first rare earth element (E) and/or the second rare earth element (D) can be basic (e.g., can exhibit some degree of basicity; can have affinity for hydrogen; can exhibit some degree of affinity for hydrogen). Nonlimiting examples of rare earth elements that can be considered basic for purposes of the disclosure herein include scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof. As will be appreciated by one of skill in the art, and with the help of this disclosure, and without wishing to be limited by theory, the OCM reaction is a multi-step reaction, wherein each step of the OCM reaction could benefit from specific OCM catalytic properties. For example, and without wishing to be limited by theory, an OCM catalyst should exhibit some degree of basicity to abstract a hydrogen from $CH_4$ to form hydroxyl groups [OH] on the OCM catalyst surface, as well as methyl radicals ($CH_3$·). Further, and without wishing to be limited by theory, an OCM catalyst should exhibit oxidative properties for the OCM catalyst to convert the hydroxyl groups [OH] from the catalyst surface to water, which can allow for the OCM reaction to continue (e.g., propagate). Further, as will be appreciated by one of skill in the art, and with the help of this disclosure, and without wishing to be limited by theory, an OCM catalyst could also benefit from properties like oxygen ion conductivity and proton conductivity, which properties can be critical for the OCM reaction to proceed at a very high rate (e.g., its highest possible rate). Further, as will be appreciated by one of skill in the art, and with the help of this disclosure, and without wishing to be limited by theory, an OCM catalyst comprising a single metal might not provide all the necessary properties for an optimum OCM reaction (e.g., best OCM reaction outcome) at the best level, and as such conducting an optimum OCM reaction may require an OCM catalyst with tailored composition in terms of metals present, wherein the different metals can have optimum properties for various OCM reaction steps, and wherein the different metals can provide synergistically for achieving the best performance for the OCM catalyst in an OCM reaction.

In an aspect, the OCM catalyst composition as disclosed herein can comprise one or more oxides of A; one or more oxides of La; one or more oxides of E; one or more oxides of D; or combinations thereof. The OCM catalyst composition can comprise one or more oxides of a metal, wherein the metal comprises A, La, and optionally E and/or D. In some aspects, the OCM catalyst composition can comprise, consist of, or consist essentially of the one or more oxides.

In an aspect, the one or more oxides can be present in the OCM catalyst composition in an amount of from about 0.01 wt. % to about 100.0 wt. %, alternatively from about 10.0 wt. % to about 90.0 wt. %, or alternatively from about 30.0 wt. % to about 70.0 wt. %, based on the total weight of the OCM catalyst composition. As will be appreciated by one of skill in the art, and with the help of this disclosure, a portion of the one or more oxides, in the presence of water, such as atmospheric moisture, can convert to hydroxides, and it is possible that the OCM catalyst composition will comprise some hydroxides, due to exposing the OCM catalyst composition comprising the one or more oxides to water (e.g., atmospheric moisture). Further, as will be appreciated by one of skill in the art, and with the help of this disclosure, a portion of the one or more oxides, in the presence of carbon dioxide, such as atmospheric carbon dioxide, can convert to carbonates, and it is possible that the OCM catalyst composition will comprise some carbonates, due to exposing the OCM catalyst composition comprising the one or more oxides to carbon dioxide (e.g., atmospheric carbon dioxide).

The one or more oxides can comprise a single metal oxide, mixtures of single metal oxides, a mixed metal oxide, mixtures of mixed metal oxides, mixtures of single metal oxides and mixed metal oxides, or combinations thereof.

The single metal oxide comprises one metal selected from the group consisting of A, La, E, and D. A single metal oxide can be characterized by the general formula $M_mO_y$; wherein M is the metal selected from the group consisting of A, La, E, and D; and wherein m and y are integers from 1 to 7, alternatively from 1 to 5, or alternatively from 1 to 3. A single metal oxide contains one and only one metal cation. Nonlimiting examples of single metal oxides suitable for use in the OCM catalyst compositions of the present disclosure include CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $W_2O_3$, $SnO_2$, and the like, or combinations thereof.

In an aspect, mixtures of single metal oxides can comprise two or more different single metal oxides, wherein the two or more different single metal oxides have been mixed together to form the mixture of single metal oxides. Mixtures of single metal oxides can comprise two or more different single metal oxides, wherein each single metal oxide can be selected from the group consisting of CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $Wo_3$, $MnO_2$, $W_2O_3$, and $SnO_2$. Nonlimiting examples of mixtures of single metal oxides suitable for use in the OCM catalyst compositions of the present disclosure include SrO—$La_2O_3$, SrO—MgO—$La_2O_3$, SrO—$Yb_2O_3$—$La_2O_3$, SrO—$Er_2O_3$—$La_2O_3$, SrO—$CeO_2$—$La_2O_3$, SrO—$MnO_2$—$La_2O_3$, SrO—$WO_3$—$W_2O_3$—$La_2O_3$, SrO—$WO_3$—$Tm_2O_3$—$La_2O_3$, SrO—$WO_3$—$Tm_2O_3$—$La_2O_3$, SrO—BaO—$CeO_2$—$Er_2O_3$—$La_2O_3$, SrO—$CeO_2$—$Ce_2O_3$—$Er_2O_3$—$La_2O_3$, SrO—BaO—$WO_3$—$W_2O_3$—$La_2O_3$, SrO—BaO—$Sm_2O_3$—$WO_3$—$W_2O_3$—$La_2O_3$, SrO—MgO—$CeO_2$—$Ce_2O_3$—$WO_3$—$W_2O_3$—$La_2O_3$, SrO—CaO—$PrO_2$—$Pr_2O_3$—MnO—$Mn_2O_3$—$La_2O_3$, and the like, or combinations thereof.

The mixed metal oxide comprises two or more different metals, wherein each metal can be independently selected from the group consisting of A, La, E, and D. A mixed metal oxide can be characterized by the general formula $M^1_{m1}M^2_{m2}O_y$; wherein $M^1$ and $M^2$ are metals; wherein each of the $M^1$ and $M^2$ can be independently selected from the group consisting of A, La, E, and D; and wherein m1, m2 and y are integers from 1 to 15, alternatively from 1 to 10, or alternatively from 1 to 7. In some aspects, $M^1$ and $M^2$ can be metal cations of different chemical elements, for example $M^1$ can be a lanthanum cation and $M^2$ can be a strontium cation. In other embodiments, $M^1$ and $M^2$ can be different cations of the same chemical element, wherein $M^1$ and $M^2$ can have different oxidation states. For example, the mixed metal oxide can comprise $Mn_3O_4$, wherein $M^1$ can be a Mn (II) cation and $M^2$ can be a Mn (III) cation. Nonlimiting examples of mixed metal oxides suitable for use in the OCM catalyst compositions of the present disclosure include La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of mixed metal oxides can comprise two or more different mixed metal oxides, wherein the two or more different mixed metal oxides have been mixed together to form the mixture of mixed metal oxides. Mixtures of mixed metal oxides can comprise two or more different mixed metal oxides, such as La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of single metal oxides and mixed metal oxides can comprise at least one single metal oxide and at least one mixed metal oxide, wherein the at least one single metal oxide and the at least one mixed metal oxide have been mixed together to form the mixture of single metal oxides and mixed metal oxides.

The OCM catalyst compositions suitable for use in the present disclosure can be supported OCM catalyst compositions and/or unsupported OCM catalyst compositions. In some aspects, the supported OCM catalyst compositions can comprise a support, wherein the support can be catalytically active (e.g., the support can catalyze an OCM reaction, such as MgO). In other aspects, the supported OCM catalyst compositions can comprise a support, wherein the support can be catalytically inactive (e.g., the support cannot catalyze an OCM reaction, such as $SiO_2$). In yet other aspects, the supported OCM catalyst compositions can comprise a catalytically active support and a catalytically inactive support. Nonlimiting examples of a support suitable for use in the present disclosure include MgO, $Al_2O_3$, $SiO_2$, $ZrO_2$, $TiO_2$, and the like, or combinations thereof. As will be appreciated by one of skill in the art, and with the help of this disclosure, the support can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In an aspect, the OCM catalyst composition can further comprise a support, wherein at least a portion of the OCM catalyst composition contacts, coats, is embedded in, is supported by, and/or is distributed throughout at least a portion of the support. In such aspect, the support can be in the form of powders, particles, pellets, monoliths, foams, honeycombs, and the like, or combinations thereof. Nonlimiting examples of support particle shapes include cylindrical, discoidal, spherical, tabular, ellipsoidal, equant, irregular, cubic, acicular, and the like, or combinations thereof.

In an aspect, the OCM catalyst composition can further comprise a porous support. As will be appreciated by one of skill in the art, and with the help of this disclosure, a porous material (e.g., support) can provide for an enhanced surface area of contact between the OCM catalyst composition and the reactant mixture, which in turn would result in a higher $CH_4$ conversion to $CH_3$.

The OCM catalyst composition can be made by using any suitable methodology. In an aspect, a method of making an OCM catalyst composition can comprise a step of forming an OCM catalyst precursor mixture, wherein the OCM catalyst precursor mixture comprises one or more compounds comprising an alkaline earth metal (A) cation, one or more compounds comprising a La cation, one or more compounds comprising a first rare earth element (E) cation, and one or more compounds comprising a redox agent cation or a second rare earth element (D) cation; and wherein the first rare earth element cation and the second rare earth element cation are different. The OCM catalyst precursor mixture can be characterized by a molar ratio of La to alkaline earth metal of b:1, wherein b is from about 0.01 to about 10.0, alternatively from about 0.1 to about 8, or alternatively from about 0.5 to about 5. The OCM catalyst precursor mixture can be characterized by a molar ratio of first rare earth element to alkaline earth metal of c:1, wherein c is from about 0 to about 10.0, alternatively from about 0.1 to about 8, or alternatively from about 0.5 to about 5. The OCM catalyst precursor mixture can be characterized by a molar ratio of redox agent or second rare earth element to alkaline earth metal of d:1, wherein d is from about 0 to about 10.0, alternatively from about 0.1 to about 8, or alternatively from about 0.5 to about 5.

The one or more compounds comprising an alkaline earth metal cation can comprise an alkaline earth metal nitrate, an alkaline earth metal oxide, an alkaline earth metal hydroxide, an alkaline earth metal chloride, an alkaline earth metal acetate, an alkaline earth metal carbonate, and the like, or combinations thereof. The one or more compounds comprising a La cation can comprise a La nitrate, a La oxide, a La hydroxide, a La chloride, a La acetate, a La carbonate, and the like, or combinations thereof. The one or more compounds comprising a first rare earth element cation can comprise a first rare earth element nitrate, a first rare earth element oxide, a first rare earth element hydroxide, a first rare earth element chloride, a first rare earth element acetate, a first rare earth element carbonate, and the like, or combinations thereof. The one or more compounds comprising a redox agent cation can comprise a redox agent nitrate, a redox agent oxide, a redox agent hydroxide, a redox agent chloride, a redox agent acetate, a redox agent carbonate, and the like, or combinations thereof. The one or more compounds comprising a second rare earth element cation can comprise a second rare earth element nitrate, a second rare earth element oxide, a second rare earth element hydroxide, a second rare earth element chloride, a second rare earth element acetate, a second rare earth element carbonate, and the like, or combinations thereof.

In an aspect, the step of forming the OCM catalyst precursor mixture can comprise (i) solubilizing the one or more compounds comprising an alkaline earth metal cation, one or more compounds comprising a La cation, one or more compounds comprising a first rare earth element cation, and one or more compounds comprising a redox agent cation or a second rare earth element cation in an aqueous medium to form an OCM catalyst precursor aqueous solution. The aqueous medium can be water, or an aqueous solution. The OCM catalyst precursor aqueous solution can be formed by dissolving the one or more compounds comprising an alkaline earth metal cation, one or more compounds comprising a La cation, one or more compounds comprising a first rare earth element cation, one or more compounds comprising a redox agent cation or a second rare earth element cation, or combinations thereof, in water or any suitable aqueous medium. As will be appreciated by one of skill in the art, and with the help of this disclosure, the one or more compounds comprising an alkaline earth metal cation, one or more compounds comprising a La cation, one or more compounds comprising a first rare earth element cation, and one or more compounds comprising a redox agent cation or a second rare earth element cation can be dissolved in an aqueous medium in any suitable order. In some aspects, the one or more compounds comprising an alkaline earth metal cation, one or more compounds comprising a La cation, one or more compounds comprising a first rare earth element cation, and one or more compounds comprising a redox agent cation or a second rare earth element cation can be first mixed together and then dissolved in an aqueous medium.

The OCM catalyst precursor aqueous solution can be dried to form the OCM catalyst precursor mixture. In an aspect, at least a portion of the OCM catalyst precursor aqueous solution can be dried at a temperature of equal to or greater than about 75° C., alternatively of equal to or greater than about 100° C., or alternatively of equal to or greater than about 125° C., to yield the OCM catalyst precursor mixture. The OCM catalyst precursor aqueous solution can be dried for a time period of equal to or greater than about 4 hours, alternatively equal to or greater than about 8 hours, or alternatively equal to or greater than about 12 hours.

In an aspect, a method of making an OCM catalyst composition can comprise a step of calcining at least a portion of the OCM catalyst precursor mixture to form the OCM catalyst composition, wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states. The OCM catalyst precursor mixture can be calcined at a temperature of equal to or greater than about 750° C., alternatively equal to or greater than about 800° C., or alternatively equal to or greater than about 900° C., to yield the OCM catalyst composition. The OCM catalyst precursor mixture can be calcined for a time period of equal to or greater than about 2 hours, alternatively equal to or greater than about 4 hours, or alternatively equal to or greater than about 6 hours.

In some aspects, at least a portion of the OCM catalyst precursor mixture can be calcined in an oxidizing atmosphere (e.g., in an atmosphere comprising oxygen, for example in air) to form the OCM catalyst composition. Without wishing to be limited by theory, the oxygen in the OCM catalyst compositions characterized by the general formula $A_aLa_bE_eD_dO_x$ can originate in the oxidizing atmosphere used for calcining the OCM catalyst precursor mixture. Further, without wishing to be limited by theory, the oxygen in the OCM catalyst compositions characterized by the general formula $A_aLa_bE_eD_dO_x$ can originate in the one or more compounds comprising an alkaline earth metal cation, one or more compounds comprising a La cation, one or more compounds comprising a first rare earth element cation, and one or more compounds comprising a redox agent cation or a second rare earth element cation, provided that at least one of these compounds comprises oxygen in its formula, as is the case with nitrates, oxides, hydroxides, acetates, carbonates, etc.

In some aspects, the method of making an OCM catalyst composition can further comprise contacting the OCM catalyst composition with a support to yield a supported catalyst (e.g., an OCM supported catalyst, an OCM supported catalyst composition, etc.).

In other aspects, the method of making an OCM catalyst composition can comprise forming the OCM catalyst composition in the presence of the support, such that the resulting OCM catalyst composition (after the calcining step) comprises the support. For example, at least a portion of the OCM catalyst precursor aqueous solution can be contacted with a support to yield a supported OCM catalyst precursor. In an aspect, at least a portion of the supported OCM catalyst precursor can be further dried (e.g., at a temperature of equal to or greater than about 75° C.) and calcined (e.g., at a temperature of equal to or greater than about 750° C.) to form the OCM catalyst composition.

In an aspect, a method for producing olefins can comprise allowing at least a portion of the reactant mixture to contact at least a portion of the OCM catalyst composition and react via an OCM reaction to form a product mixture comprising olefins.

The product mixture comprises coupling products, partial oxidation products (e.g., deep oxidation products, partial conversion products, such as CO, $H_2$, $CO_2$), and unreacted methane. The coupling products can comprise olefins (e.g., alkenes, characterized by a general formula $C_nH_{2n}$) and paraffins (e.g., alkanes, characterized by a general formula $C_nH_{2n+2}$).

The product mixture can comprise $C_{2+}$ hydrocarbons, wherein the $C_{2+}$ hydrocarbons can comprise $C_2$ hydrocarbons and $C_3$ hydrocarbons. In an aspect, the $C_{2+}$ hydrocarbons can further comprise $C_4$ hydrocarbons ($C_4$s), such as for example butane, iso-butane, n-butane, butylene, etc. The $C_2$ hydrocarbons can comprise ethylene ($C_2H_4$) and ethane ($C_2H_6$). The $C_2$ hydrocarbons can further comprise acetylene ($C_2H_2$). The $C_3$ hydrocarbons can comprise propylene ($C_3H_6$) and propane ($C_3H_8$).

In an aspect, the OCM catalyst composition as disclosed herein can be characterized by a $CH_4$ conversion that is increased by equal to or greater than about 1%, alternatively equal to or greater than about 2%, alternatively equal to or greater than about 5%, or alternatively equal to or greater than about 10%, when compared to a $CH_4$ conversion of an otherwise similar OCM catalyst composition (i) without La, or (ii) comprising an alkaline earth metal and La in a La to the alkaline earth metal molar ratio other than from about 0.01:1 to about 10.0:1. Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. For example, the methane conversion can be calculated by using equation (1):

$$CH_4 \text{ conversion} = \frac{C^{in}_{CH_4} - C^{out}_{CH_4}}{C^{in}_{CH_4}} \times 100\% \qquad (1)$$

wherein $C^{in}_{CH_4}$=number of moles of C from $CH_4$ that entered the reactor as part of the reactant mixture; and $C^{out}_{CH_4}$ number of moles of C from $CH_4$ that was recovered from the reactor as part of the product mixture.

In an aspect, the $O_2$ conversion for the OCM as disclosed herein can be equal to or greater than about 90%, alternatively equal to or greater than about 95%, alternatively equal to or greater than about 99%, alternatively equal to or greater than about 99.9%, or alternatively about 100%. As will be appreciated by one of skill in the art, and with the help of this disclosure, the reactant mixture in OCM reactions is generally characterized by a methane to oxygen molar ratio of greater than 1:1, and as such the $O_2$ conversion is fairly high in OCM processes, most often approaching 90%-100%. Without wishing to be limited by theory, oxygen is usually a limiting reagent in OCM processes. The oxygen conversion can be calculated by using equation (2):

$$O_2 \text{ conversion} = \frac{O^{in}_2 - O^{out}_2}{O^{in}_2} \times 100\% \qquad (2)$$

wherein $O^{in}_2$=number of moles of $O_2$ that entered the reactor as part of the reactant mixture; and $O^{out}_2$=number of moles of $O_2$ that was recovered from the reactor as part of the product mixture.

In an aspect, the OCM catalyst composition as disclosed herein can be characterized by a reactor temperature effective for achieving an $O_2$ conversion of equal to or greater than about 90% that is decreased by equal to or greater than about 25° C., alternatively by equal to or greater than about 50° C., alternatively by equal to or greater than about 75° C., or alternatively by equal to or greater than about 100° C., when compared to a reactor temperature effective for achieving an $O_2$ conversion of equal to or greater than about 90% of an otherwise similar OCM catalyst composition (i) without La, or (ii) comprising an alkaline earth metal and La in a La to the alkaline earth metal molar ratio other than from about 0.01:1 to about 10.0:1.

In some aspects, the OCM catalyst composition as disclosed herein can be characterized by a reactor temperature effective for achieving an $O_2$ conversion of equal to or greater than about 90% of less than about 700° C., alternatively less than about 600° C., or alternatively less than about 500° C. As will be appreciated by one of skill in the art, and with the help of this disclosure, the reactor temperature effective for achieving an $O_2$ conversion of equal to or greater than about 90% is dependent upon specific reactor conditions, such as for example methane to oxygen molar ratio, type and size of reactor, GHSV, etc.

In an aspect, the OCM catalyst composition as disclosed herein can be characterized by a $C_{2+}$ selectivity that is increased by equal to or greater than about 2%, alternatively equal to or greater than about 5%, alternatively equal to or greater than about 10%, alternatively equal to or greater than about 15%, or alternatively equal to or greater than about 20%, when compared to a $C_{2+}$ selectivity of an otherwise similar OCM catalyst composition (i) without La, or (ii) comprising an alkaline earth metal and La in a La to the alkaline earth metal molar ratio other than from about 0.01:1 to about 10.0:1.

Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a C selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc) $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc.

A $C_{2+}$ selectivity (e.g., selectivity to $C_{2+}$ hydrocarbons) refers to how much $C_2H_4$, $C_3H_6$, $C_2H_2$, $C_2H_6$, $C_3H_8$, and $C_4$s were formed divided by the total products formed, including $C_2H_4$, $C_3H_6$, $C_2H_2$, $C_2H_6$, $C_3H_8$, $C_4$s, $CO_2$ and CO. For example, the $C_{2+}$ selectivity can be calculated by using equation (3):

$$C_{2+} \text{ selectivity} = \frac{2C_{C_2H_4} + 2C_{C_2H_6} + 2C_{C_2H_2} + 3C_{C_3H_6} + 3C_{C_3H_8} + 4C_{C_{4s}}}{2C_{C_2H_4} + 2C_{C_2H_6} + 2C_{C_2H_2} + 3C_{C_3H_6} + 3C_{C_3H_8} + 4C_{C_{4s}} + C_{CO_2} + C_{CO}} \times 100\% \quad (3)$$

As will be appreciated by one of skill in the art, and with the help of this disclosure, if a specific product and/or hydrocarbon product is not produced in a certain OCM reaction/process, then the corresponding $C_{Cx}$ is 0, and the term is simply removed from selectivity calculations.

Without wishing to be limited by theory, when the selectivity (e.g., $C_{2+}$ selectivity) of an OCM process increases, less methane is converted to undesirable products, such as deep oxidation products (e.g., CO, $CO_2$), which in turn means that more oxygen (which is often the limiting reagent in OCM processes) is available for the conversion of methane to desirable products (e.g., $C_2$ products, $C_2H_4$, $C_{2+}$ products, etc.), thus enabling the increased $C_{2-}$ selectivity. As will be appreciated by one of skill in the art, and with the help of this disclosure, the higher the temperature in the reactor, the more deep oxidation products will be produced, and as such lower temperatures for achieving an $O_2$ conversion of equal to or greater than about 90% will lead to a lower amount of deep oxidation products produced, thus resulting in the increased methane conversion to the desirable products.

In some aspects, the OCM catalyst composition as disclosed herein can be characterized by a $CH_4$ conversion that is increased by equal to or greater than about 1%, alternatively equal to or greater than about 2%, alternatively equal to or greater than about 5%, or alternatively equal to or greater than about 10%; and by a $C_{2+}$ selectivity that is increased by equal to or greater than about 2%, alternatively equal to or greater than about 5%, alternatively equal to or greater than about 10%, alternatively equal to or greater than about 15%, or alternatively equal to or greater than about 20%; when compared to a $CH_4$ conversion and a $C_{2+}$ selectivity, respectively, of an otherwise similar OCM catalyst composition (i) without La, or (ii) comprising an alkaline earth metal and La in a La to the alkaline earth metal molar ratio other than from about 0.01:1 to about 10.0:1. As will be appreciated by one of skill in the art, and with the help of this disclosure, increasing the $CH_4$ conversion at the same time with increasing the $C_{2+}$ selectivity can occur when the increased methane conversion is not due to increased deep oxidation reactions, but to conversion to desired products, such as $C_{2+}$ products produced via OCM reactions.

In an aspect, a method for producing olefins can comprise recovering at least a portion of the product mixture from the reactor. In an aspect, a method for producing olefins can comprise recovering at least a portion of the $C_2$ hydrocarbons from the product mixture. The product mixture can comprise $C_{2+}$ hydrocarbons (including olefins), unreacted methane, and optionally a diluent. The water produced from the OCM reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

In an aspect, at least a portion of the $C_{2+}$ hydrocarbons can be separated (e.g., recovered) from the product mixture to yield recovered $C_{2+}$ hydrocarbons. The $C_{2+}$ hydrocarbons can be separated from the product mixture by using any suitable separation technique. In an aspect, at least a portion of the $C_{2+}$ hydrocarbons can be separated from the product mixture by distillation (e.g., cryogenic distillation).

In an aspect, at least a portion of the recovered $C_{2+}$ hydrocarbons can be used for ethylene production. In some aspects, at least a portion of ethylene can be separated from the product mixture (e.g., from the $C_{2+}$ hydrocarbons, from the recovered $C_{2+}$ hydrocarbons) to yield recovered ethylene and recovered hydrocarbons, by using any suitable separation technique (e.g., distillation). In other aspects, at least a portion of the recovered hydrocarbons (e.g., recovered $C_{2+}$ hydrocarbons after olefin separation, such as separation of $C_2H_4$ and $C_3H_6$) can be converted to ethylene, for example by a conventional steam cracking process.

A method for producing olefins can comprise recovering at least a portion of the olefins from the product mixture. In an aspect, at least a portion of the olefins can be separated from the product mixture by distillation (e.g., cryogenic distillation). As will be appreciated by one of skill in the art, and with the help of this disclosure, the olefins are generally individually separated from their paraffin counterparts by distillation (e.g., cryogenic distillation). For example, ethylene can be separated from ethane by distillation (e.g., cryogenic distillation). As another example, propylene can be separated from propane by distillation (e.g., cryogenic distillation).

In an aspect, at least a portion of the unreacted methane can be separated from the product mixture to yield recovered methane. Methane can be separated from the product mixture by using any suitable separation technique, such as for example distillation (e.g., cryogenic distillation). At least a portion of the recovered methane can be recycled to the reactant mixture.

In an aspect, the OCM catalyst composition can be characterized by the general formula $Sr_aLa_bYb_cCe_dO_x$; wherein a is 1.0; wherein b is from about 0.01 to about 10.0, alternatively from about 0.1 to about 8, or alternatively from about 0.5 to about 5; wherein c is from about 0.01 to about 10.0, alternatively from about 0.1 to about 8, or alternatively from about 0.5 to about 5; wherein d is from about 0.01 to about 10.0, alternatively from about 0.1 to about 8, or alternatively from about 0.5 to about 5; and wherein x balances the oxidation states. As will be appreciated by one of the skill in the art, and with the help of this disclosure, at least some of the Sr, La, Yb and Ce can have multiple oxidation states within the OCM catalyst composition, and as such x can have any suitable value that allows for the oxygen anions to balance all the cations.

In another aspect, the OCM catalyst composition can be characterized by the general formula $Sr_aLa_bYb_cTm_dO_x$; wherein a is 1.0; wherein b is from about 0.01 to about 10.0, alternatively from about 0.1 to about 8, or alternatively from about 0.5 to about 5; wherein c is from about 0.01 to about 10.0, alternatively from about 0.1 to about 8, or alternatively from about 0.5 to about 5; wherein d is from about 0.01 to about 10.0, alternatively from about 0.1 to about 8, or alternatively from about 0.5 to about 5; and wherein x balances the oxidation states. As will be appreciated by one of the skill in the art, and with the help of this disclosure, at least some of the Sr, La, Yb and Tm can have multiple oxidation states within the OCM catalyst composition, and as such x can have any suitable value that allows for the oxygen anions to balance all the cations.

In yet another aspect, the OCM catalyst composition can be characterized by the general formula $A_aLa_bO_x$; wherein A is an alkaline earth metal; wherein a is 1.0; wherein b is from about 0.01 to about 10.0, alternatively from about 0.1 to about 8, or alternatively from about 0.5 to about 5; and wherein x balances the oxidation states. As will be appreciated by one of skill in the art, and with the help of this disclosure, A and/or La could have multiple oxidation states within the OCM catalyst composition, and as such x can have any suitable value that allows for the oxygen anions to balance all the cations.

In an aspect of the OCM catalyst composition characterized by the general formula $A_aLa_bO_x$, A is Sr. In such aspect, the OCM catalyst composition can be characterized by the general formula $Sr_aLa_bO_x$; wherein a is 1.0; wherein b is from about 0.01 to about 10.0, alternatively from about 0.1 to about 8, or alternatively from about 0.5 to about 5; and wherein x balances the oxidation states.

In still yet another aspect, the OCM catalyst composition can be characterized by the general formula $A_aLa_bE_cO_x$; wherein A is an alkaline earth metal; wherein E is a first rare earth element; wherein a is 1.0; wherein b is from about 0.01 to about 10.0, alternatively from about 0.1 to about 8, or alternatively from about 0.5 to about 5; wherein c is from about 0.01 to about 10.0, alternatively from about 0.1 to about 8, or alternatively from about 0.5 to about 5; and wherein x balances the oxidation states. As will be appreciated by one of the skill in the art, and with the help of this disclosure, at least some of the A, La, and E can have multiple oxidation states within the OCM catalyst composition, and as such x can have any suitable value that allows for the oxygen anions to balance all the cations.

In an aspect of the OCM catalyst composition characterized by the general formula $A_aLa_bE_cO_x$, A is Sr, and E is Yb. In such aspect, the OCM catalyst composition can be characterized by the general formula $Sr_aLa_bYb_cO_x$; wherein a is 1.0; wherein b is from about 0.01 to about 10.0, alternatively from about 0.1 to about 8, or alternatively from about 0.5 to about 5; wherein c is from about 0.01 to about 10.0, alternatively from about 0.1 to about 8, or alternatively from about 0.5 to about 5; and wherein x balances the oxidation states.

In still yet another aspect, the OCM catalyst composition can be characterized by the general formula $A_aLa_bD_dO_x$; wherein A is an alkaline earth metal; wherein D is a redox agent; wherein a is 1.0; wherein b is from about 0.01 to about 10.0, alternatively from about 0.1 to about 8, or alternatively from about 0.5 to about 5; wherein d is from about 0.01 to about 10.0, alternatively from about 0.1 to about 8, or alternatively from about 0.5 to about 5; and wherein x balances the oxidation states. As will be appreciated by one of the skill in the art, and with the help of this disclosure, at least some of the A, La, and D can have multiple oxidation states within the OCM catalyst composition, and as such x can have any suitable value that allows for the oxygen anions to balance all the cations.

In an aspect of the OCM catalyst composition characterized by the general formula $A_aLa_bD_dO_x$, A is Sr, and D is Mn. In such aspect, the OCM catalyst composition can be characterized by the general formula $Sr_aLa_bMn_dO_x$; wherein a is 1.0; wherein b is from about 0.01 to about 10.0, alternatively from about 0.1 to about 8, or alternatively from about 0.5 to about 5; wherein d is from about 0.01 to about 10.0, alternatively from about 0.1 to about 8, or alternatively from about 0.5 to about 5; and wherein x balances the oxidation states.

In an aspect of the OCM catalyst composition characterized by the general formula $A_aLa_bD_dO_x$, A is Sr, and D is W. In such aspect, the OCM catalyst composition can be characterized by the general formula $Sr_aLa_bW_dO_x$; wherein a is 1.0; wherein b is from about 0.01 to about 10.0, alternatively from about 0.1 to about 8, or alternatively from about 0.5 to about 5; wherein d is from about 0.01 to about 10.0, alternatively from about 0.1 to about 8, or alternatively from about 0.5 to about 5; and wherein x balances the oxidation states.

In an aspect, a method of making an OCM catalyst composition can comprise the steps of (a) forming an OCM catalyst precursor aqueous solution comprising an alkaline earth metal nitrate, a La nitrate, a first rare earth element nitrate, and a redox agent nitrate or a second rare earth element nitrate; wherein the first rare earth element nitrate and the second rare earth element nitrate are different; wherein the OCM catalyst precursor aqueous solution is characterized by a molar ratio of La to alkaline earth metal of b:1, wherein b is from about 0.01 to about 10.0; wherein the OCM catalyst precursor aqueous solution is characterized by a molar ratio of first rare earth element to alkaline earth metal of c:1, wherein c is from about 0 to about 10.0; and wherein the OCM catalyst precursor aqueous solution is characterized by a molar ratio of redox agent or second rare earth element to alkaline earth metal of d:1, wherein d is from about 0 to about 10.0; (b) drying at least a portion of the OCM catalyst precursor aqueous solution at a temperature of about 125° C. for about 12-18 h to form an OCM catalyst precursor mixture; and (c) calcining at least a portion of the OCM catalyst precursor mixture at a temperature of about 900° C. for about 4-8 h, for example in an oxidizing atmosphere, to form the OCM catalyst composition, wherein the OCM catalyst composition is characterized by the general formula $A_aLa_bE_eD_dO_x$; wherein a is 1.0; wherein b is from about 0.01 to about 10.0; wherein c is from about 0 to about 10.0; wherein d is from about 0 to about 10.0; and wherein x balances the oxidation states.

In an aspect, a method for producing ethylene can comprise the steps of (a) introducing a reactant mixture to a reactor comprising an OCM catalyst composition; wherein the reactant mixture comprises $CH_4$ and $O_2$; wherein the OCM catalyst composition is characterized by the general formula $A_aLa_bE_eD_dO_x$; wherein a is 1.0; wherein b is from about 0.01 to about 10.0; wherein c is from about 0 to about 10.0; wherein d is from about 0 to about 10.0; and wherein x balances the oxidation states; (b) allowing at least a portion of the reactant mixture to contact at least a portion of the OCM catalyst composition and react via an OCM reaction to form a product mixture comprising olefins, wherein the olefins comprise ethylene; (c) recovering at least a portion of the product mixture from the reactor; and (d) recovering at least a portion of the ethylene from the product mixture.

In an aspect, the OCM catalyst compositions characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states; and methods of making and using same, as disclosed herein can advantageously display improvements in one or more composition characteristics when compared to an otherwise similar OCM catalyst composition (i) without La, or (ii) comprising an alkaline earth metal and La in a La to the alkaline earth metal molar ratio other than from about 0.01:1 to about 10.0:1.

The OCM catalyst compositions characterized by the general formula $A_aLa_bE_eD_dO_x$; wherein a is 1.0; wherein b is from about 0.01 to about 10.0; wherein c is from about 0 to about 10.0; wherein d is from about 0 to about 10.0; and wherein x balances the oxidation states; can display improved conversion and selectivity, when compared to the conversion and selectivity, respectively, of an otherwise similar OCM catalyst composition (i) without La, or (ii) comprising an alkaline earth metal and La in a La to the alkaline earth metal molar ratio other than from about 0.01:1 to about 10.0:1. As will be appreciated by one of skill in the art, and with the help of this disclosure, high selectivity of a catalyst for methane conversion to $C_{2+}$ products via OCM is critical for commercialization of the OCM process. Without wishing to be limited by theory, a highly selective catalyst, such as the OCM catalysts disclosed herein, can advantageously reduce the heat produced in the process, such that the reactor can be easier to control and operate. Further, without wishing to be limited by theory, a highly active catalyst (in terms of conversion) can advantageously lead to a lower reactor volume, as well as a lower reaction temperature, which in turn can allow for lowering the temperature of a feed to the reactor. As will be appreciated by one of skill in the art, and with the help of this disclosure, some conventional OCM catalysts, such as the $Mn-Na_2WO_4/SiO_2$ catalyst, require for the feed to the reactor to be pre-heated to about 800° C., which translates in a high energy cost, as well as expensive specialized materials for a heat exchanger used for pre-heating the reactor feed.

In an aspect, the composition of OCM catalyst compositions characterized by the general formula $A_aLa_bE_eD_dO_x$; wherein a is 1.0; wherein b is from about 0.01 to about 10.0; wherein c is from about 0 to about 10.0; wherein d is from about 0 to about 10.0; and wherein x balances the oxidation states; as disclosed herein can be advantageously adjusted as necessary, based on the needs of the OCM reaction, to meet target criteria, such as a target selectivity and/or a target conversion, owing to a broader range of A, La, E and D content; and as such the OCM catalyst compositions as disclosed herein can display better performance when compared to otherwise similar OCM catalyst compositions (i) without La, or (ii) comprising an alkaline earth metal and La in a La to the alkaline earth metal molar ratio other than from about 0.01:1 to about 10.0:1.

The OCM catalyst compositions characterized by the general formula $A_aLa_bE_eD_dO_x$; wherein a is 1.0; wherein b is from about 0.01 to about 10.0; wherein c is from about 0 to about 10.0; wherein d is from about 0 to about 10.0; and wherein x balances the oxidation states; can advantageously display an enhanced stability of performance (e.g., in terms of conversion and selectivity) over time when compared to the stability of performance of an otherwise similar OCM catalyst composition (i) without La, or (ii) comprising an alkaline earth metal and La in a La to the alkaline earth metal molar ratio other than from about 0.01:1 to about 10.0:1. For example, the OCM catalyst compositions characterized by the general formula $A_aLa_bE_eD_dO_x$ as disclosed herein can maintain improved conversion and selectivity over a time frame that is greater than a time frame where an otherwise similar OCM catalyst composition (i) without La, or (ii) comprising an alkaline earth metal and La in a La to the alkaline earth metal molar ratio other than from about 0.01:1 to about 10.0:1, can maintain its conversion and selectivity values. As will be appreciated by one of skill in the art, and with the help of this disclosure, over time, the performance of catalysts can degrade (e.g., decay), owing to catalyst deactivation; and the longer a catalyst can maintain a desired performance (e.g., in terms of conversion and selectivity), the better the catalyst is. Additional advantages of the OCM catalyst compositions characterized by the general formula $A_aLa_bE_eD_dO_x$; wherein a is 1.0; wherein b is from about 0.01 to about 10.0; wherein c is from about 0 to about 10.0;

wherein d is from about 0 to about 10.0; and wherein x balances the oxidation states; and methods of making and using same, as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

Oxidative coupling of methane (OCM) catalyst compositions were prepared as follows.

A reference catalyst composition (reference catalyst #1) following the general formula $Sr_{1.0}Ce_{0.9}Yb_{0.1}O$ was prepared as follows. In an attempt to produce 10 g of $Sr_{1.0}Ce_{0.9}Yb_{0.1}O$, 4.23 g of $Sr(NO_3)_2$, 7.82 g of $Ce(NO_3)_3 \times 6H_2O$ and 0.90 g of $Yb(NO_3)_3 \times 5H_2O$ were added into 25 ml deionized (DI) water to provide a mixture, which mixture was further agitated until all solids were dissolved and a clear solution was obtained. The obtained clear solution was dried at 125° C. overnight to produce a dried OCM catalyst precursor mixture. The dried OCM catalyst precursor mixture was calcined under air flow at 900° C. for 6 hours to produce the reference catalyst #1 (e.g., $Sr_{1.0}Ce_{0.9}Yb_{0.1}O$ catalyst).

Other catalysts containing La were prepared as follows, and their performance was compared to the performance of the reference catalyst #1 (e.g., $Sr_{1.0}Ce_{0.9}Yb_{0.1}O$ catalyst). In an attempt to produce 10 g of catalyst #3 ($Sr_{1.0}La_{0.9}Yb_{0.1}O$ catalyst), 4.02 g of $Sr(NO_3)_2$, 7.40 g of $La(NO_3)_3 \times 6H_2O$ and 0.85 g of $Yb(NO_3)_3 \times 5H_2O$ were added into 25 ml deionized (DI) water to provide a mixture, which mixture was further agitated until all solids were dissolved and a clear solution was obtained. The obtained clear solution was dried at 125° C. overnight to produce a dried OCM catalyst precursor mixture. The dried OCM catalyst precursor mixture was calcined under air flow at 900° C. for 6 hours to produce catalyst #3 (e.g., $Sr_{1.0}La_{0.9}Yb_{0.1}O$ catalyst). Other catalysts (e.g., catalysts #1, #2, #4, #5, #6, and #7) with different amounts of La as compared to catalyst #3 were prepared in a similar fashion, but with using different amounts of $La(NO_3)_3 \times 6H_2O$, as necessary.

Catalysts containing both La and Ce (e.g., catalysts #8, and #9), and well as catalysts containing both La and Tm (e.g., catalysts #10, and #11) were prepared in a manner similar to preparing the reference catalyst #1 and catalyst #3, by using the corresponding amounts of $La(NO_3)_3 \times 6H_2O$, $Ce(NO_3)_3 \times 6H_2O$, and Tm nitrate, as necessary to obtain a catalyst with the desired general formula.

Example 2

The performance of the OCM catalyst compositions prepared as described in Example 1 was investigated.

OCM reactions were conducted by using catalysts prepared as described in Example 1 as follows. A mixture of methane and oxygen along with an internal standard, an inert gas (neon) were fed to a quartz reactor with an internal diameter (I.D.) of 2.3 mm heated by traditional clamshell furnace. A catalyst (e.g., catalyst bed) loading was 20 mg or 10 mg, and a total flow rate of reactants was 40 standard cubic centimeters per minute (sccm). The reactor was first heated to a desired temperature under an inert gas flow and then a desired gas mixture was fed to the reactor. All OCM reactions were conducted at a methane to oxygen ($CH_4:O_2$) molar ratio of 7.4 and at a reactor temperature of 750° C. The products obtained from the OCM reaction were analyzed by using an online Agilent 7890 gas chromatograph (GC) with a thermal conductivity detector (TCD) and a flame ionization detector (FID).

Methane conversion, oxygen conversion, and $C_{2+}$ selectivity were calculated according to equations (1)-(3). The performance differences between the catalysts are demonstrated in Tables 1-4.

TABLE 1

| | Catalyst composition | $CH_4$ conversion, % | $O_2$ conversion, % | $C_{2+}$ selectivity, % | Temp. (C.)* |
|---|---|---|---|---|---|
| Reference Catalyst #1 | $Sr_{1.0}Ce_{0.9}Yb_{0.1}O_x$ | 16.6 | 93.1 | 73.7 | 750 |
| Catalyst #1 | $Sr_{1.0}La_{0.3}Yb_{0.1}O_x$ | 19.7 | 83.9 | 80.7 | 775 |
| Catalyst #2 | $Sr_{1.0}La_{0.5}Yb_{0.1}O_x$ | 21.3 | 95.5 | 80.1 | 750 |
| Catalyst #3 | $Sr_{1.0}La_{0.9}Yb_{0.1}O_x$ | 21.5 | 98.3 | 81.0 | 725 |
| Catalyst #4 | $Sr_{1.0}La_{1.2}Yb_{0.1}O_x$ | 21.4 | 100.0 | 80.2 | 650 |
| Catalyst #5 | $Sr_{1.0}La_{1.5}Yb_{0.1}O_x$ | 21.2 | 100.0 | 78.0 | 650 |

*Reactor temperature at which $O_2$ conversion first reaches 90%+.

TABLE 2

| | Catalyst composition | $CH_4$ conversion, % | $O_2$ conversion, % | $C_{2+}$ selectivity, % | Temp. (C.)* |
|---|---|---|---|---|---|
| Catalyst #4 | $Sr_{1.0}La_{1.2}Yb_{0.1}O_x$ | 21.4 | 100.0 | 80.2 | 650 |
| Catalyst #5 | $Sr_{1.0}La_{1.5}Yb_{0.1}O_x$ | 21.2 | 100.0 | 78.0 | 650 |
| Catalyst #6 | $Sr_{1.0}La_{1.8}Yb_{0.1}O_x$ | 20.9 | 98.0 | 79.6 | 675 |
| Catalyst #7 | $Sr_{1.0}La_{2.0}Yb_{0.1}O_x$ | 20.4 | 97.2 | 79.0 | 700 |

*Reactor temperature at which $O_2$ conversion first reaches 90%+.

TABLE 3

| | Catalyst composition | CH$_4$ conversion, % | O$_2$ conversion, % | C$_{2+}$ selectivity, % | Temp. (C.)* |
|---|---|---|---|---|---|
| Reference Catalyst #1 | Sr$_{1.0}$Ce$_{0.9}$Yb$_{0.1}$O$_x$ | 16.6 | 93.1 | 73.7 | 750 |
| Catalyst #8 | Sr$_{1.0}$Ce$_{0.5}$La$_{0.5}$Yb$_{0.1}$O$_x$ | 18.4 | 81.9 | 78.3 | 775 |
| Catalyst #9 | Sr$_{1.0}$Ce$_{0.3}$La$_{0.7}$Yb$_{0.1}$O$_x$ | 21.1 | 98.5 | 80.1 | 725 |

*Reactor temperature at which O$_2$ conversion first reaches 90%+.

TABLE 4

| | Catalyst composition | CH$_4$ conversion, % | O$_2$ conversion, % | C$_{2+}$ selectivity, % | Temp. (C.)* |
|---|---|---|---|---|---|
| Reference Catalyst #1 | Sr1.0Ce0.9Yb0.1Ox | 16.6 | 93.1 | 73.7 | 750 |
| Example 10 | Sr1.0La0.9Tm0.1Yb0.1Ox | 20.9 | 98.4 | 79.8 | 700 |
| Example 11 | Sr1.0La0.9Tm0.2Yb0.1Ox | 22.4 | 97.9 | 81.3 | 700 |

*Reactor temperature at which O$_2$ conversion first reaches 90%+.

The data in Table 1 (catalyst loading 20 mg) indicate that higher activity (e.g., in terms of conversion) and higher selectivity was obtained with the La containing catalysts (#1, #2, #3, #4, and #5) when compared to the reference catalyst #1. For high La containing catalysts, like catalysts #4 and #5, catalyst loading of 10 mg was also tested, along with other high La containing catalysts (#6 and #7), and their performance is shown in Table 2. Even with the lower catalyst loading (10 mg as opposed to 20 mg), high performances were obtained for catalysts with a high La content, such as catalysts #4, #5, #6, and #7.

The data in Table 3 further indicate that La containing catalysts (#8 and #9) display better performance than the reference catalyst #1. From the data in Table 3 it can be seen that some Ce in addition to La in the catalysts (#8 and #9) increases the CH$_4$ conversion, as well as the C$_{2+}$ selectivity.

The data in Table 4 further indicate that La and Tm containing catalysts (#10 and #11) display better performance than the reference catalyst #1, in terms of increased CH$_4$ conversion, as well as increased C$_{2+}$ selectivity. By comparing to catalysts #10 and #11 to catalyst #3, it can be seen that introducing Tm into the catalyst increases catalyst activity, in terms of CH$_4$ conversion, as well as C$_{2+}$ selectivity.

Example 3

The performance of catalyst #3 prepared as described in Example 1 was further investigated. OCM reactions were conducted as described in Example 2, at a reactor temperature of 800° C., and the stability of the catalyst was recorded over a period of more than 60 hours, in terms of O$_2$ conversion (displayed in Figure #1); and CH$_4$ conversion and C$_{2+}$ selectivity (displayed in FIG. 2). As displayed in FIGS. 1 and 2, catalyst #3 displayed stable performance over the tested time period, in terms of conversion and selectivity.

The performance of catalyst #3 was further compared with the performance of an extensively studied catalyst, Mn—Na$_2$WO$_4$/SiO$_2$ (reference catalyst #2), in order to demonstrate advantages of the OCM catalyst compositions disclosed herein. Reference catalyst #2 was prepared by using the following method described below.

Silica gel (18.6 g, Davisil® Grade 646) was used after drying overnight. Mn(NO$_3$)$_2$·4H$_2$O (1.73 g) was dissolved in deionized water (18.6 mL), and then added dropwise onto the silica gel. The resulting manganese impregnated silica material was dried overnight. Na$_2$WO$_4$·4H$_2$O (1.13 g) was dissolved in deionized water (18.6 mL), and the solution obtained was added onto the dried manganese silica material above. The resulting material obtained was dried overnight at 125° C., and then calcined at 800° C. for 6 hours under airflow to obtain the Mn—Na$_2$WO$_4$/SiO$_2$ catalyst (the reference catalyst #2).

A stability test of the reference catalyst #2 was conducted as follows. A mixture of methane and oxygen along with an internal standard, an inert gas (argon) were fed to a quartz reactor with an internal diameter (I.D.) of 5.0 mm heated by traditional clamshell furnace. A catalyst (e.g., catalyst bed) loading was 250 mg, and a total flow rate of reactants was 100 standard cubic centimeters per minute (sccm). The reactor was first heated to a desired temperature under an inert gas flow and then a desired gas mixture was fed to the reactor. All OCM reactions were conducted at a methane to oxygen (CH$_4$:O$_2$) molar ratio of 7.4 and at a reactor temperature of 825° C.

Figure 2:
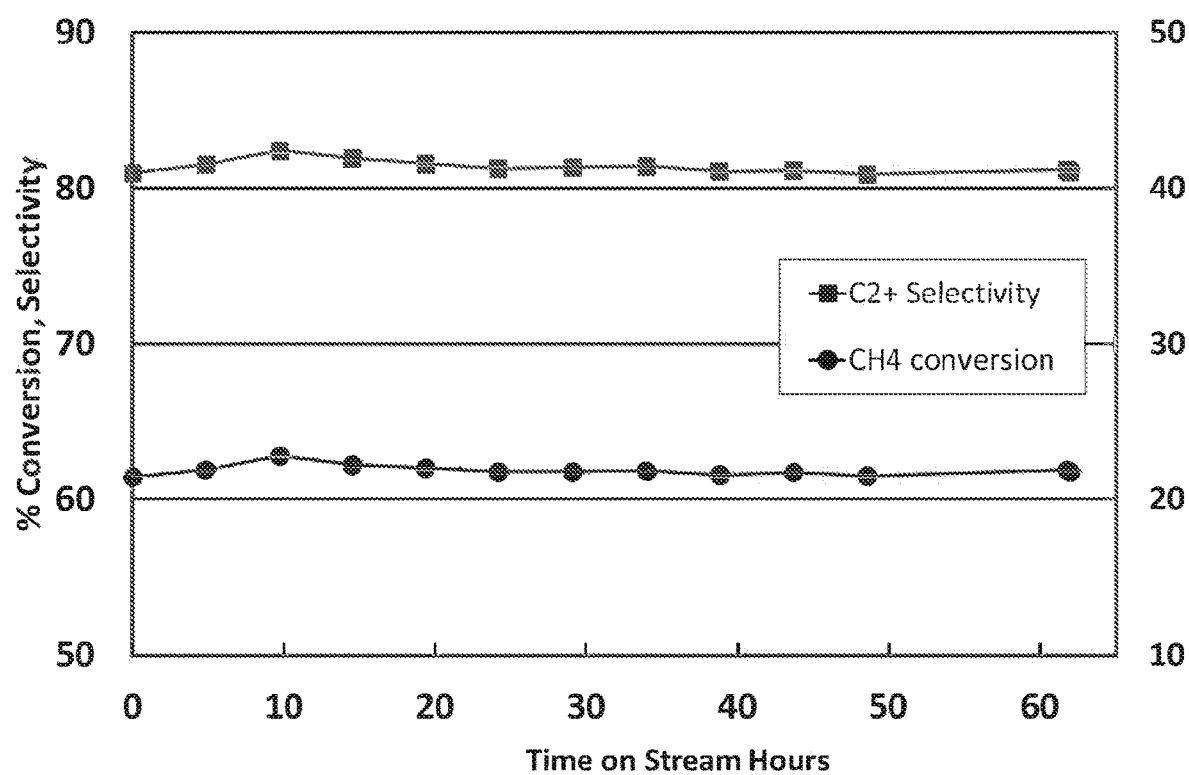
FIG. 2 displays a graph of $CH_4$ conversion, and $C_{2+}$ selectivity in an OCM reaction over time.

The oxygen conversion obtained with the reference catalyst #2 was also displayed in FIG. 1, along with the oxygen conversion data for catalyst #3, over the same time period. It can be seen that fast decline of performance in terms of O$_2$ conversion was observed with the reference catalyst #2, while catalyst #3 displayed a stable O$_2$ conversion of about 100% across the entire testing period (over 60 hours). Thus, it can be concluded that the OCM catalyst compositions disclosed herein (catalyst #3) have a clear advantage over conventional catalysts (reference catalyst #2) in terms of performance stability.

The data in Examples 1-3 indicate that the metals (A, La, E, and D) present in the OCM catalysts compositions as disclosed herein display synergetic effects in terms of conversion and selectivity, wherein high activity (e.g., conversion) and high selectivity were obtained for the OCM catalysts prepared as disclosed herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first aspect, which is an oxidative coupling of methane (OCM) catalyst composition characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

A second aspect, which is the OCM catalyst composition of the first aspect, wherein the alkaline earth metal is selected from the group consisting of magnesium (Mg), calcium (Ca), strontium (Sr), barium (Ba), and combinations thereof.

A third aspect, which is the OCM catalyst composition of any one of the first and the second aspects, wherein the first rare earth element and the second rare earth element can each independently be selected from the group consisting of scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

A fourth aspect, which is the OCM catalyst composition of any one of the first through the third aspects, wherein the redox agent is selected from the group consisting of manganese (Mn), tungsten (W), bismuth (Bi), antimony (Sb), tin (Sn), cerium (Ce), praseodymium (Pr), and combinations thereof.

A fifth aspect, which is the OCM catalyst composition of any one of the first through the fourth aspects comprising one or more oxides of A; one or more oxides of La; one or more oxides of E; one or more oxides of D; or combinations thereof.

A sixth aspect, which is the OCM catalyst composition of any one of the first through the fifth aspects having the general formula $Sr_aLa_bYb_cCe_dO_x$; wherein a is 1.0; wherein b is from about 0.01 to about 10.0; wherein c is from about 0.01 to about 10.0; wherein d is from about 0.01 to about 10.0; and wherein x balances the oxidation states.

A seventh aspect, which is the OCM catalyst composition of any one of the first through the fifth aspects having the general formula $Sr_aLa_bYb_cTm_dO_x$; wherein a is 1.0; wherein b is from about 0.01 to about 10.0; wherein c is from about 0.01 to about 10.0; wherein d is from about 0.01 to about 10.0; and wherein x balances the oxidation states.

An eighth aspect, which is the OCM catalyst composition of any one of the first through the fifth aspects having the general formula $A_aLa_bO_x$; wherein A is an alkaline earth metal; wherein a is 1.0; wherein b is from about 0.01 to about 10.0; and wherein x balances the oxidation states.

A ninth aspect, which is the OCM catalyst composition of the eighth aspect having the general formula $Sr_aLa_bO_x$; wherein a is 1.0; wherein b is from about 0.01 to about 10.0; and wherein x balances the oxidation states.

A tenth aspect, which is the OCM catalyst composition of any one of the first through the fifth aspects having the general formula $A_aLa_bE_cO_x$; wherein A is an alkaline earth metal; wherein E is a first rare earth element; wherein a is 1.0; wherein b is from about 0.01 to about 10.0; wherein c is from about 0.01 to about 10.0; and wherein x balances the oxidation states.

An eleventh aspect, which is the OCM catalyst composition of the tenth aspect having the general formula $Sr_aLa_bYb_cO_x$; wherein a is 1.0; wherein b is from about 0.01 to about 10.0; wherein c is from about 0.01 to about 10.0; and wherein x balances the oxidation states.

A twelfth aspect, which is the OCM catalyst composition of any one of the first through the fifth aspects having the general formula $A_aLa_bD_dO_x$; wherein A is an alkaline earth metal; wherein D is a redox agent; wherein a is 1.0; wherein b is from about 0.01 to about 10.0; wherein d is from about 0.01 to about 10.0; and wherein x balances the oxidation states.

A thirteenth aspect, which is the OCM catalyst composition of the twelfth aspect having the general formula $Sr_aLa_bMn_dO_x$; wherein a is 1.0; wherein b is from about 0.01 to about 10.0; wherein d is from about 0.01 to about 10.0; and wherein x balances the oxidation states.

A fourteenth aspect, which is the OCM catalyst composition of the twelfth aspect having the general formula $Sr_aLa_bW_dO_x$; wherein a is 1.0; wherein b is from about 0.01 to about 10.0; wherein d is from about 0.01 to about 10.0; and wherein x balances the oxidation states.

A fifteenth aspect, which is the OCM catalyst composition of any one of the first through the fourteenth aspects further comprising a support, wherein at least a portion of the OCM catalyst composition contacts, coats, is embedded in, is supported by, and/or is distributed throughout at least a portion of the support; wherein the support comprises MgO, $Al_2O_3$, $SiO_2$, $ZrO_2$, $TiO_2$, or combinations thereof; and wherein the support is in the form of powders, particles, pellets, monoliths, foams, honeycombs, or combinations thereof.

A sixteenth aspect, which is the OCM catalyst composition of any one of the first through the fifteenth aspects, wherein the OCM catalyst composition is characterized by a $C_{2+}$ selectivity that is increased by equal to or greater than about 2%, when compared to a $C_{2+}$ selectivity of an otherwise similar OCM catalyst composition (i) without La, or (ii) comprising an alkaline earth metal and La in a La to the alkaline earth metal molar ratio other than from about 0.01:1 to about 10.0:1.

A seventeenth aspect, which is the OCM catalyst composition of any one of the first through the sixteenth aspects, wherein the OCM catalyst composition is characterized by a $CH_4$ conversion that is increased by equal to or greater than about 1%, when compared to a $CH_4$ conversion of an otherwise similar OCM catalyst composition (i) without La, or (ii) comprising an alkaline earth metal and La in a La to the alkaline earth metal molar ratio other than from about 0.01:1 to about 10.0:1.

An eighteenth aspect, which is the OCM catalyst composition of any one of the first through the seventeenth aspects, wherein the OCM catalyst composition is characterized by a reactor temperature effective for achieving an $O_2$ conversion of equal to or greater than about 90% that is decreased by equal to or greater than about 25° C., when compared to a reactor temperature effective for achieving an $O_2$ conversion of equal to or greater than about 90% of an otherwise similar OCM catalyst composition (i) without La, or (ii) comprising an alkaline earth metal and La in a La to the alkaline earth metal molar ratio other than from about 0.01:1 to about 10.0:1.

A nineteenth aspect, which is a method of making an oxidative coupling of methane (OCM) catalyst composition comprising (a) forming an OCM catalyst precursor mixture; wherein the OCM catalyst precursor mixture comprises one or more compounds comprising an alkaline earth metal cation, one or more compounds comprising a La cation, one or more compounds comprising a first rare earth element cation, and one or more compounds comprising a redox agent cation or a second rare earth element cation; wherein the first rare earth element cation and the second rare earth element cation are different; wherein the OCM catalyst precursor mixture is characterized by a molar ratio of La to alkaline earth metal of b:1, wherein b is from about 0.01 to about 10.0; wherein the OCM catalyst precursor mixture is characterized by a molar ratio of first rare earth element to alkaline earth metal of c:1, wherein c is from about 0 to about 10.0; and wherein the OCM catalyst precursor mixture is characterized by a molar ratio of redox agent or second rare earth element to alkaline earth metal of d:1, wherein d is from about 0 to about 10.0; and (b) calcining at least a portion of the OCM catalyst precursor mixture to form the OCM catalyst composition, wherein the OCM catalyst composition is characterized by the general formula $A_a La_b E_e D_d O_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

A twentieth aspect, which is the method of the nineteenth aspect, wherein the step (a) of forming an OCM catalyst precursor mixture further comprises (i) solubilizing the one or more compounds comprising an alkaline earth metal cation, one or more compounds comprising a La cation, one or more compounds comprising a first rare earth element cation, and one or more compounds comprising a redox agent cation or a second rare earth element cation in an aqueous medium to form an OCM catalyst precursor aqueous solution; and (ii) drying at least a portion of the OCM catalyst precursor aqueous solution to form the OCM catalyst precursor mixture.

A twenty-first aspect, which is the method of the twentieth aspect, wherein the OCM catalyst precursor aqueous solution is dried at a temperature of equal to or greater than about 75° C.

A twenty-second aspect, which is the method of any one of the nineteenth through the twenty-first aspects, wherein at least a portion of the OCM catalyst precursor aqueous solution is contacted with a support to yield a supported OCM catalyst precursor.

A twenty-third aspect, which is the method of the twenty-second aspect, wherein at least a portion of the supported OCM catalyst precursor is further dried and calcined to form the OCM catalyst composition.

A twenty-fourth aspect, which is the method of any one of the nineteenth through the twenty-third aspects, wherein the OCM catalyst precursor mixture is calcined at a temperature of equal to or greater than about 750° C.

A twenty-fifth aspect, which is the method of any one of the nineteenth through the twenty-fourth aspects, wherein the one or more compounds comprising an alkaline earth metal cation comprises an alkaline earth metal nitrate, an alkaline earth metal oxide, an alkaline earth metal hydroxide, an alkaline earth metal chloride, an alkaline earth metal acetate, an alkaline earth metal carbonate, or combinations thereof; wherein the one or more compounds comprising a La cation comprises a La nitrate, a La oxide, a La hydroxide, a La chloride, a La acetate, a La carbonate, or combinations thereof; wherein the one or more compounds comprising a first rare earth element cation comprises a first rare earth element nitrate, a first rare earth element oxide, a first rare earth element hydroxide, a first rare earth element chloride, a first rare earth element acetate, a first rare earth element carbonate, or combinations thereof; wherein the one or more compounds comprising a redox agent cation comprises a redox agent nitrate, a redox agent oxide, a redox agent hydroxide, a redox agent chloride, a redox agent acetate, a redox agent carbonate, or combinations thereof; and wherein the one or more compounds comprising a second rare earth element cation comprises a second rare earth element nitrate, a second rare earth element oxide, a second rare earth element hydroxide, a second rare earth element chloride, a second rare earth element acetate, a second rare earth element carbonate, or combinations thereof.

A twenty-sixth aspect, which is an OCM catalyst produced by the method of any one of the nineteenth through the twenty-fifth aspects.

A twenty-seventh aspect, which is a method of making an oxidative coupling of methane (OCM) catalyst composition comprising (a) forming an OCM catalyst precursor aqueous solution comprising an alkaline earth metal nitrate, a La nitrate, a first rare earth element nitrate, and a redox agent nitrate or a second rare earth element nitrate; wherein the first rare earth element nitrate and the second rare earth element nitrate are different; wherein the OCM catalyst precursor aqueous solution is characterized by a molar ratio of La to alkaline earth metal of b:1, wherein b is from about 0.01 to about 10.0; wherein the OCM catalyst precursor aqueous solution is characterized by a molar ratio of first rare earth element to alkaline earth metal of c:1, wherein c is from about 0 to about 10.0; and wherein the OCM catalyst precursor aqueous solution is characterized by a molar ratio of redox agent or second rare earth element to alkaline earth metal of d:1, wherein d is from about 0 to about 10.0; (b) drying at least a portion of the OCM catalyst precursor aqueous solution at a temperature of equal to or greater than about 75° C. to form an OCM catalyst precursor mixture; and (c) calcining at least a portion of the OCM catalyst precursor mixture at a temperature of equal to or greater than about 750° C. to form the OCM catalyst composition, wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

A twenty-eighth aspect, which is an oxidative coupling of methane (OCM) catalyst composition produced by (a) solubilizing one or more compounds comprising an alkaline earth metal cation, one or more compounds comprising a La cation, one or more compounds comprising a first rare earth element cation, and one or more compounds comprising a redox agent cation or second rare earth element cation in an aqueous medium to form an OCM catalyst precursor aqueous solution; wherein the first rare earth element cation and the second rare earth element cation are different; wherein the OCM catalyst precursor aqueous solution is characterized by a molar ratio of La to alkaline earth metal of b:1, wherein b is from about 0.01 to about 10.0; wherein the OCM catalyst precursor aqueous solution is characterized by a molar ratio of first rare earth element to alkaline earth metal of c:1, wherein c is from about 0 to about 10.0; and wherein the OCM catalyst precursor aqueous solution is characterized by a molar ratio of redox agent or second rare earth element to alkaline earth metal of d:1, wherein d is from about 0 to about 10.0; (b) drying at least a portion of the OCM catalyst precursor aqueous solution at a temperature of equal to or greater than about 75° C. to form an OCM catalyst precursor mixture; and (c) calcining at least a portion of the OCM catalyst precursor mixture at a temperature of equal to or greater than about 750° C. to form the OCM catalyst composition, wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

A twenty-ninth aspect, which is a method for producing olefins comprising (a) introducing a reactant mixture to a reactor comprising an oxidative coupling of methane (OCM) catalyst composition; wherein the reactant mixture comprises methane ($CH_4$) and oxygen ($O_2$); wherein the OCM catalyst composition is characterized by the general formula $A_aLa_bE_eD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states; (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture.

A thirtieth aspect, which is the method of the twenty-ninth aspect, wherein the reactor is characterized by a reactor temperature effective for achieving an $O_2$ conversion of equal to or greater than about 90% that is decreased by equal to or greater than about 25° C., when compared to a reactor temperature effective for achieving an $O_2$ conversion of equal to or greater than about 90% of a reactor comprising an otherwise similar OCM catalyst composition (i) without La, or (ii) comprising an alkaline earth metal and La in a La to the alkaline earth metal molar ratio other than from about 0.01:1 to about 10.0:1.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. An oxidative coupling of methane (OCM) catalyst composition characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

2. The OCM catalyst composition of claim 1, wherein the alkaline earth metal is selected from the group consisting of magnesium (Mg), calcium (Ca), strontium (Sr), barium (Ba), and combinations thereof.

3. The OCM catalyst composition of claim 1, wherein the first rare earth element and the second rare earth element can each independently be selected from the group consisting of scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

4. The OCM catalyst composition of claim 1, wherein the redox agent is selected from the group consisting of manganese (Mn), tungsten (W), bismuth (Bi), antimony (Sb), tin (Sn), cerium (Ce), praseodymium (Pr), and combinations thereof.

5. The OCM catalyst composition of claim 1 comprising one or more oxides of A; one or more oxides of La; one or more oxides of E; one or more oxides of D; or combinations thereof.

6. The OCM catalyst composition of claim 1 having the general formula $Sr_aLa_bYb_cCe_dO_x$; wherein a is 1.0; wherein b is from about 0.01 to about 10.0; wherein c is from about 0.01 to about 10.0; wherein d is from about 0.01 to about 10.0; and wherein x balances the oxidation states.

7. The OCM catalyst composition of claim 1 having the general formula $Sr_aLa_bYb_cTm_dO_x$; wherein a is 1.0; wherein b is from about 0.01 to about 10.0; wherein c is from about 0.01 to about 10.0; wherein d is from about 0.01 to about 10.0; and wherein x balances the oxidation states.

8. The OCM catalyst composition of claim 1 having the general formula $A_aLa_bO_x$; wherein A is an alkaline earth metal; wherein a is 1.0; wherein b is from about 0.01 to about 10.0; and wherein x balances the oxidation states.

9. The OCM catalyst composition of claim 8 having the general formula $Sr_aLa_bO_x$; wherein a is 1.0; wherein b is from about 0.01 to about 10.0; and wherein x balances the oxidation states.

10. The OCM catalyst composition of claim 1 having the general formula $A_aLa_bE_cO_x$; wherein A is an alkaline earth metal; wherein E is a first rare earth element; wherein a is 1.0; wherein b is from about 0.01 to about 10.0; wherein c is from about 0.01 to about 10.0; and wherein x balances the oxidation states.

11. The OCM catalyst composition of claim 10 having the general formula $Sr_aLa_bYb_cO_x$; wherein a is 1.0; wherein b is from about 0.01 to about 10.0; wherein c is from about 0.01 to about 10.0; and wherein x balances the oxidation states.

12. The OCM catalyst composition of claim 1 having the general formula $A_aLa_bD_dO_x$; wherein A is an alkaline earth metal; wherein D is a redox agent; wherein a is 1.0; wherein b is from about 0.01 to about 10.0; wherein d is from about 0.01 to about 10.0; and wherein x balances the oxidation states.

13. The OCM catalyst composition of claim 1, wherein (1) the OCM catalyst composition is characterized by a $C_{2+}$ selectivity that is increased by equal to or greater than about 2%, when compared to a $C_{2+}$ selectivity of an otherwise identical OCM catalyst composition (i) without La, or (ii) comprising an alkaline earth metal and La in a La to the alkaline earth metal molar ratio other than from about 0.01:1 to about 10.0:1; and wherein (2) the OCM catalyst composition is characterized by a $CH_4$ conversion that is increased by equal to or greater than about 1%, when compared to a $CH_4$ conversion of an otherwise identical OCM catalyst composition (i) without La, or (ii) comprising an alkaline earth metal and La in a La to the alkaline earth metal molar ratio other than from about 0.01:1 to about 10.0:1.

14. The OCM catalyst composition of claim 1, wherein the OCM catalyst composition is characterized by a reactor temperature effective for achieving an $O_2$ conversion of equal to or greater than about 90% that is decreased by equal to or greater than about 25° C., when compared to a reactor temperature effective for achieving an $O_2$ conversion of equal to or greater than about 90% of an otherwise identical OCM catalyst composition (i) without La, or (ii) comprising an alkaline earth metal and La in a La to the alkaline earth metal molar ratio other than from about 0.01:1 to about 10.0:1.

15. A method of making an oxidative coupling of methane (OCM) catalyst composition comprising:
(a) forming an OCM catalyst precursor mixture; wherein the OCM catalyst precursor mixture comprises one or more compounds comprising an alkaline earth metal cation, one or more compounds comprising a La cation, one or more compounds comprising a first rare earth element cation, and one or more compounds comprising a redox agent cation or a second rare earth element cation; wherein the first rare earth element cation and the second rare earth element cation are different; wherein the OCM catalyst precursor mixture is characterized by a molar ratio of La to alkaline earth metal of b:1, wherein b is from about 0.01 to about 10.0; wherein the OCM catalyst precursor mixture is characterized by a molar ratio of first rare earth element to alkaline earth metal of c:1, wherein c is from about 0 to about 10.0; and wherein the OCM catalyst precursor mixture is characterized by a molar ratio of redox agent or second rare earth element to alkaline earth metal of d:1, wherein d is from about 0 to about 10.0; and
(b) calcining at least a portion of the OCM catalyst precursor mixture to form the OCM catalyst composition, wherein the OCM catalyst composition is characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states.

16. The method of claim 15, wherein the step (a) of forming an OCM catalyst precursor mixture further comprises (i) solubilizing the one or more compounds comprising an alkaline earth metal cation, one or more compounds comprising a La cation, one or more compounds comprising a first rare earth element cation, and one or more compounds comprising a redox agent cation or a second rare earth element cation in an aqueous medium to form an OCM catalyst precursor aqueous solution; and (ii) drying at least a portion of the OCM catalyst precursor aqueous solution at a temperature of equal to or greater than about 75° C. to form the OCM catalyst precursor mixture.

17. The method of claim 15, wherein the OCM catalyst precursor mixture is calcined at a temperature of equal to or greater than about 750° C.

18. The method of claim 15, wherein the one or more compounds comprising an alkaline earth metal cation comprises an alkaline earth metal nitrate, an alkaline earth metal oxide, an alkaline earth metal hydroxide, an alkaline earth metal chloride, an alkaline earth metal acetate, an alkaline earth metal carbonate, or combinations thereof; wherein the one or more compounds comprising a La cation comprises a La nitrate, a La oxide, a La hydroxide, a La chloride, a La acetate, a La carbonate, or combinations thereof; wherein the one or more compounds comprising a first rare earth element cation comprises a first rare earth element nitrate, a first rare earth element oxide, a first rare earth element hydroxide, a first rare earth element chloride, a first rare earth element acetate, a first rare earth element carbonate, or combinations thereof; wherein the one or more compounds comprising a redox agent cation comprises a redox agent nitrate, a redox agent oxide, a redox agent hydroxide, a redox agent chloride, a redox agent acetate, a redox agent carbonate, or combinations thereof; and wherein the one or more compounds comprising a second rare earth element cation comprises a second rare earth element nitrate, a second rare earth element oxide, a second rare earth element hydroxide, a second rare earth element chloride, a second rare earth element acetate, a second rare earth element carbonate, or combinations thereof.

19. An OCM catalyst produced by the method of claim 15.

20. A method for producing olefins comprising:
(a) introducing a reactant mixture to a reactor comprising an oxidative coupling of methane (OCM) catalyst composition; wherein the reactant mixture comprises methane ($CH_4$) and oxygen ($O_2$); wherein the OCM catalyst composition is characterized by the general formula $A_aLa_bE_cD_dO_x$; wherein A is an alkaline earth metal; wherein E is a first rare earth element; wherein D is a redox agent or a second rare earth element; wherein the first rare earth element and the second rare earth element are different; wherein a is 1.0; wherein b is from about 0.01 to about 10.0; wherein c is from about 0 to about 10.0; wherein d is from about 0 to about 10.0; and wherein x balances the oxidation states;

(b) allowing at least a portion of the reactant mixture to contact at least a portion of the OCM catalyst composition and react via an OCM reaction to form a product mixture comprising olefins;

(c) recovering at least a portion of the product mixture from the reactor; and (d) recovering at least a portion of the olefins from the product mixture.

* * * * *